(12) United States Patent
Bourgeois et al.

(10) Patent No.: US 11,759,210 B1
(45) Date of Patent: Sep. 19, 2023

(54) METHOD AND SYSTEM FOR DISTRACTION NEUROGENESIS

(71) Applicant: Axsonus LLC, San Antonio, TX (US)

(72) Inventors: Jason Bourgeois, San Antonio, TX (US); Michael L. Wach, Alpharetta, GA (US); Frank Lau, New Orleans, LA (US)

(73) Assignee: Axsonus LLC, San Antonio, TX (US)

( * ) Notice: Subject to any disclaimer, the term of this patent is extended or adjusted under 35 U.S.C. 154(b) by 1,082 days.

(21) Appl. No.: 16/503,550

(22) Filed: Jul. 4, 2019

Related U.S. Application Data

(60) Provisional application No. 62/693,952, filed on Jul. 4, 2018.

(51) Int. Cl.
| | |
|---|---|
| *A61B 17/11* | (2006.01) |
| *A61N 1/05* | (2006.01) |
| *A61N 1/20* | (2006.01) |
| *A61B 5/00* | (2006.01) |
| *A61N 1/36* | (2006.01) |
| *A61B 17/02* | (2006.01) |
| *A61M 5/142* | (2006.01) |
| *A61N 1/32* | (2006.01) |
| *A61K 45/06* | (2006.01) |
| *A61B 17/34* | (2006.01) |
| *C07K 14/475* | (2006.01) |
| *A61B 90/00* | (2016.01) |
| *A61B 17/00* | (2006.01) |

(52) U.S. Cl.
CPC .......... *A61B 17/1128* (2013.01); *A61B 5/4041* (2013.01); *A61B 17/0218* (2013.01); *A61M 5/142* (2013.01); *A61N 1/0551* (2013.01); *A61N 1/205* (2013.01); *A61N 1/36071* (2013.01); *A61B 17/3468* (2013.01); *A61B 90/03* (2016.02); *A61B 2017/00022* (2013.01); *A61B 2017/00398* (2013.01); *A61B 2017/1103* (2013.01); *A61B 2017/1132* (2013.01); *A61B 2090/064* (2016.02); *A61K 45/06* (2013.01); *A61L 2300/414* (2013.01); *A61L 2430/32* (2013.01); *A61L 2430/38* (2013.01); *A61N 1/326* (2013.01); *C07K 14/475* (2013.01)

(58) Field of Classification Search
CPC .... A61N 1/05; A61N 1/20; A61N 1/36; A61B 17/11; A61B 5/00
See application file for complete search history.

(56) References Cited

U.S. PATENT DOCUMENTS

| | | | | |
|---|---|---|---|---|
| 8,162,979 | B2* | 4/2012 | Sachs et al. | A61B 17/7041 606/264 |
| 2003/0225442 | A1* | 12/2003 | Saadat | A61F 7/12 607/105 |
| 2019/0298417 | A1* | 10/2019 | Barrett et al. | A61B 17/7041 |

\* cited by examiner

*Primary Examiner* — Christopher J Beccia
(74) *Attorney, Agent, or Firm* — Ascenda Law Group, PC

(57) ABSTRACT

To achieve in vivo repair of severed mammalian nerve tissue, a system can be employed to induce distraction neurogenesis. At least a portion of the system can be anchored at an injury site, such as between distal and proximal nerve ends. The system can be attached to the proximal nerve end and can place the nerve under micro-tension for an extended period of treatment. The system may also deliver medication or treatment to encourage neurogenesis and to reduce pain in the subject receiving treatment. After the course of treatment, the device can be removed from the injury site, and the nerve ends rejoined.

15 Claims, 10 Drawing Sheets

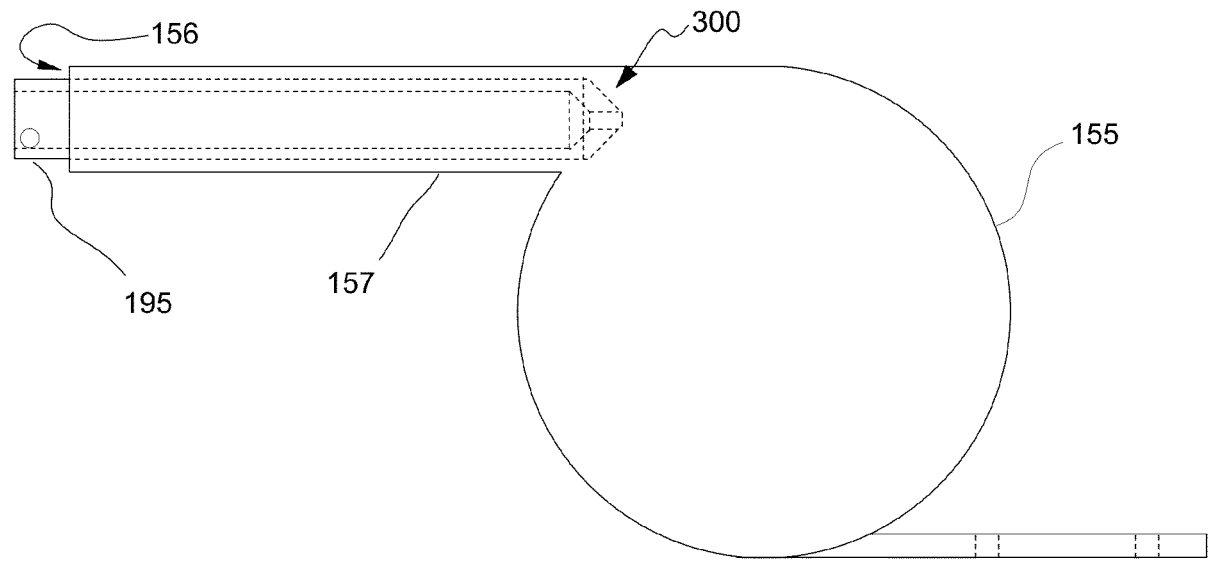
FIG. 3A
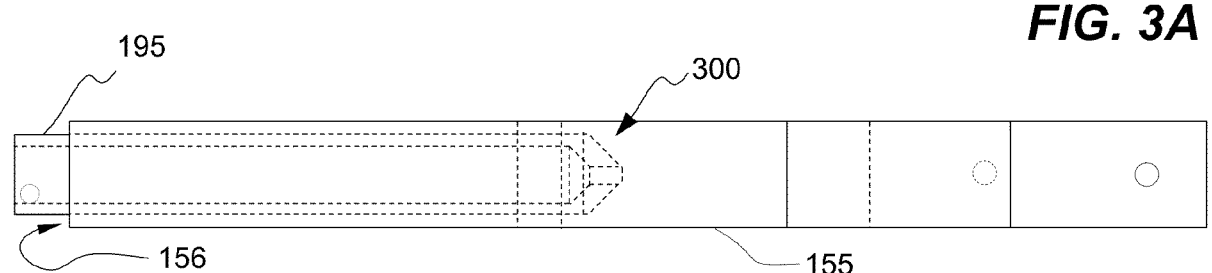
FIG. 3B
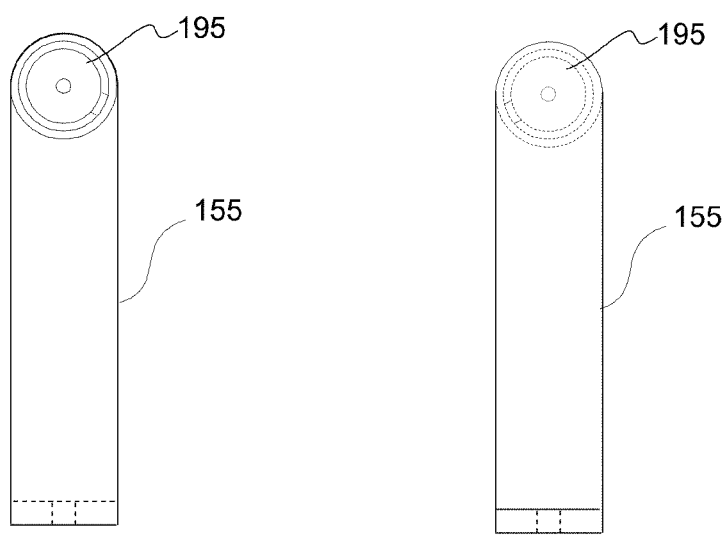
FIG. 3C    FIG. 3D

METHOD AND SYSTEM FOR DISTRACTION NEUROGENESIS

CROSS REFERENCE TO RELATED APPLICATIONS

This application claims priority to U.S. Provisional Pat. Application No. 62/693,952 filed Jul. 4, 2018 in the name of Jason Keshav Emile Bourgeois and entitled "SYSTEM FOR DISTAL DISTRACTION OF SEVERED PERIPHERAL NERVES," the entire contents of which are hereby incorporated herein by reference.

TECHNICAL FIELD

Embodiments of the technology relate generally to regenerating tissue and more particularly to using distraction to stimulate nerve regeneration.

BACKGROUND

Injuries to peripheral nerves may result from trauma, surgery, cancer, or congenital anomalies, to name a few representative causes. Injuries to peripheral nerves can be also caused by radiation therapy, chemotherapy, metabolic/endocrine complications, inflammatory and autoimmune diseases, vitamin deficiencies, infectious diseases, toxic causes, accidental exposure to organic metals and heavy metals, drugs, amputations, and disease or condition relating to a loss of motor or sensory nerve function. Nerve injury may include lesion, nerve transection, crush, compression, stretch, laceration (sharps or bone fragments), ischemia, and blast. In addition, nerve injury or lesion may result from damage or disruption of neuronal axons.

Peripheral nerve injury ("PNI") is a major source of morbidity and an area with significant medical need. Indeed, only about 50 percent of patients achieve good to normal restoration of function following conventional surgical repair, regardless of the strategy. Moreover, failure of nerve regeneration may necessitate amputation of an otherwise salvaged limb. This frequently stems from inadequacy of current PNI repair strategies, where even the "gold-standard" treatment—the nerve autograft-is largely ineffective for major nerve trauma, typically characterized as loss of a large segment of nerve (for example, greater than 5 cm) or injury occurring closer to the spinal cord (for example, shoulder or thigh) resulting in extremely long distances for axon regeneration to distal targets (for example, hand or foot). As a result, the field is in need of a transformative technology for repair of peripheral nerve injury.

Nerve guidance conduits (NGCs) can connect the proximal and distal ends of some injured nerves and provide a microenvironment for regeneration of axons. Nerve growth factor (NGF), a protein released from in-growing Schwann cells, has been studied widely and purported to have biological activities in the development and maintenance of sensory, sympathetic and central neurons. During the process of nerve regeneration, the development of axons may be supported by NGF. In some instances, NGF within NGCs can significantly enhance the morphological and functional recovery of repaired nerves. NGF, like many other growth factors, has a low stability in physiological conditions and thus can have limited effectiveness in conventional application. The key point of the design of NGF-loaded NGC is to maintain NGF release and the activity of NGF over the long duration of nerve regeneration.

Nerve allografts can also be used to connect the proximal and distal ends of the injured nerve and allow the axons to grow across a nerve gap. Allografts are produced by processing nerves harvested from human cadaveric donors.

Basic fibroblast growth factor (b-FGF) has also been shown to enhance the in vitro survival and neurite extension of various types of neurons including dorsal root ganglia (DRG) cells. Alpha-1 glycoprotein (α1-GP), an acute phase reactant, has been reported to enhance in vitro neuron growth. When added to a collagen-filled nerve guide, purified acidic fibroblast growth factor (aFGF) may increase the number of myelinated axons that regenerate across a 5-mm nerve gap distance. In addition, a greater number of primary sensory and motor neurons may extend axons through the nerve guide in animals treated with aFGF. Thus, the effect of aFGF on peripheral nerve regeneration does not appear to be simply an increase in axonal branching within the nerve guide tube. IGF-I administered to the dorsal root ganglia or locally around a crush lesion can regenerate sensory fibers. This effect can be inhibited if the nerve is perfused with specific antibodies to native IGF-I. Thus, endogenous extracellular IGF-I may also play a role during regeneration of peripheral nerve fibers. Exogenously administered insulin-like growth factor II can also increase the rate of peripheral nerve regeneration, and endogenous insulin-like growth factors in nerves support a normal rate of regeneration. Insulin-like growth factor II gene expression typically correlates with synapse development.

Administration of immunosuppressive pharmaceuticals (e.g. tacrolimus) can reduce the collagen fiber content and scar area in nerve anastomosis of a nerve injury. Tacrolimus can also significantly increase myelinated nerve fiber density, average axon diameter, and myelin sheath thickness. Administration of some immunosuppressants can lead to a significant increase in the recovery rate of nerve function after nerve injury. Other pharmaceuticals such as hyaluronic acid can exhibit similar reduction in scar formation when administered to the site of a nerve injury. In a related concept, the suppression of chondroitin sulfate proteoglycans found in the extracellular matrix of nerves can enhance nerve regeneration. Intraneural administration of chondroitinase can suppress the action of chondroitin sulfate proteoglycans thus resulting in enhanced nerve regeneration after injury or allotransplantation without reducing laminin modulated regeneration. The outgrowth of neurites from neurons can be induced by the extracellular matrix glycoproteins, fibronectin and laminin, and by polyomithine-binding neurite-promoting factors (NPFs).

Other therapeutic modalities, including physical medicine, can improve the regeneration rate of injured nerves. Electrical stimulation of the parent axons proximal to a repair site can substantially reduce the period of axonal outgrowth and accelerate preferential motor reinnervation (PMR). The positive effect of short-term electrical stimulation is mediated via the cell body, implicating an enhanced growth program. Electrical stimulation may also be employed at a distal nerve stump to abrogate Schwann cell death and improve long-term outcomes in a post-operative setting. Another therapeutic modality, hyperbaric oxygen, has shown favorable effects on healing of mechanically damaged peripheral nerves induced by nerve transection, crushing injury, or both. Hyperbaric oxygen has also been reported to have benefits to the peripheral and central nervous systems, mainly because of improvement in microcirculation, as mechanical compression destroys nerve blood supply leaving the nerve anoxic and stopping axonal transport. Hyperbaric oxygen may also increase the number of Schwann cells, producing a variety of trophic factors that participate in nerve regeneration. Further, cold therapy and vibration have been shown to reduce pain sensations. These therapies may work to modulate the signals through the action of fast, non-noxious motion nerves blocking the afferent pain-receptive nerves.

Biologics such as bone marrow stromal cells (MSCs), multipotent stem calls, can be induced to differentiate into cells with Schwann cell characteristics capable of potentiating peripheral nervous system regeneration. MSCs treated with beta-mercaptoethanol followed by retinoic acid and cultured in the presence of forskolin, basic-FGF, PDGF and heregulin, can change morphologically into cells resembling primary cultured Schwann cells. When these cells are transplanted into nerve lesion sites, the injured nerves can demonstrate rapid nerve fiber regeneration. MSCs are able to differentiate into myelinating cells, capable of supporting nerve fiber regrowth, and they can therefore be applied to induce nerve regeneration.

Neuroactive steroids, like progesterone (P) and its metabolites, i.e., dihydro-progesterone (DHP) and tetrahydroprogesterone (THP), dehydroepiandrosterone, estrogens, androgens, etc., can exert neuroprotective effects in the neuronal and nonneuronal compartments of the nervous system. For instance, estrogens in the PNS can exert different effects on sensory and autonomic neurons, influencing development, plasticity, and repair of DRG neurons, and also controlling the neuritogenesis of sympathetic neurons and the proliferation of Schwann cells. Further, neuroactive steroids such as P, DHP, and THP can modulate mitogenic activity, proliferation, and synthesis of peripheral myelin proteins by Schwann cells. In this context, while P and DHP act via the classic progesterone receptor (PR), THP is a potent allosteric modulator of GABA-A. However, Schwann cells are a target but also a source of neuroactive steroids. Similarly, Mitogen-activated protein Kinases (MAPKs) are components of the pathways controlling cell proliferation, differentiation, and death. During cell damage or nerve regeneration, MAPKs are expressed in sensory neurons and in Schwann cells. MAPK inhibitors such as the p38 blocker SD-169 may enhance axonal regeneration by interfering with proinflammatory cytokine expression and inhibiting neuronal and Schwann cell apoptosis. Other pharmaceutical therapies such as modified glutamate, Erythropoietin, delta-9-tetrahydrocannabinol (THC), GABA, and acetyl-choline can modulate neuron regeneration.

An emerging nerve repair technique is nerve fusion with polyethylene glycol (PEG). The putative mechanism of this approach is immediate sealing of the disrupted axonal cell membrane with PEG. Limited data suggest that this restores axonal continuity and therefore nerve function, particularly in small animals, but clinical data have been less successful.

A limitation of conventional strategies to functionally repair major nerve trauma lies in a lack of ability to coax a sufficient number of axons to grow a substantial distance quickly enough to reinnervate distal targets (for example, muscles and skin) before function is permanently lost. The more proximal the nerve injury, the greater this challenge becomes. To overcome such limitations, need exists for repair strategies to encourage supraphysiological regeneration of proximal axons, for example greater than a millimeter in 24 hours. Need further exists for maintenance of the pro-regenerative capacity of the distal nerve segment for regenerating axons.

Often, following long or proximal PNI, the pro-regenerative environment fails and there is incomplete functional recovery. For example, a patient with a PNI of the upper arm may regain elbow, but not hand function, due to the distance between the nerve injury and the end targets in the hand, which are often not reached by proximal axons before the distal environment is no longer pro-regenerative (e.g. scarring/loss of distal nerve) or the nerve targets are lost (e.g. degeneration of the motor end plate in muscles). For example, suppose upper-arm trauma results in extraction of a six-centimeter segment of nerve, so that six centimeters of gap separates a proximal nerve end from a distal nerve end. With typical conventional approaches, by the time the proximal end of the proximal nerve end grows sufficiently for rejoining with the distal nerve end (if it at all), the condition of the injured person's hand may have diminished to a non-recoverable level. In another example, a PNI may be untreatable due to the large size of the nerve lesion or injury, irrespective of the lesion or injury location.

Various techniques for improving the pro-regenerative capacity of the distal nerve segment following nerve injury have been explored. These include providing neurotrophic factors (e.g., GDNF, BDNF, and TGF-beta) to the distal nerve segment; administering electrical stimulation to the nerve sheath in an attempt to stimulate acceleration of axon regeneration; and transferring a foreign sensory nerve or an adjacent healthy nerve to the denervated nerve sheath (known as "babysitting" techniques). However, such techniques are often limited by a lack of efficacy, particularly with regard to long-term efficacy. In addition, some of these techniques have the clear disadvantage of sacrificing a healthy nearby nerve for the purpose of transferring it to the adjacent denervated nerve stump.

Thus, there is a need in the art for effective means of accelerating the rate of axonal growth beyond the physiologic rate, which has been reported as approximately 1 mm / 24 hours in a typical human. There is furthermore a need in the art for more effective means of maintaining the pro-regenerative capacity of denervated distal nerve segments, so that the effectiveness of current or future means of PNI repair can be increased. A capability fulfilling this need, or a related deficiency in the art, could improve healthcare of neurological medical conditions and/or benefit neurology and other branches of medicine involving nerves and other injured tissues.

While certain novel features of this invention shown and described below are pointed out in the claims, the invention is not intended to be limited to the details specified, since a person of ordinary skill in the relevant art will understand that various omissions, modifications, substitutions and changes in the forms of details of the invention illustrated and in its operation may be made without departing in any way from the spirit of the present invention. No feature of the invention is critical or essential unless it is expressly stated as being "critical" or "essential".

SUMMARY

A device can distract a peripheral nerve by applying tension to an end of the nerve. The resulting distraction can produce, stimulate, maintain, or encourage nerve growth or regeneration. The device can comprise a system. In certain aspects of the disclosure, the system can comprise one or more of a drive, a retractor, a regulator, a controller, a coupler, a reel, a line, and an energy storage device, not necessarily as distinct elements.

In certain aspects of the disclosure, a device comprising a tensioning apparatus, a suture or other means for connecting to a nerve stump, a pharmaceutical or treatment delivery modality, a bracket, and a case may be attached to the proximal or distal end of a transected nerve in order to encourage neurogenesis. The tensioning apparatus may be disposed within the case, the bracket may be disposed on the outer surface of the case, the suture or other means for connecting to a nerve stump may pass through an aperture in the case, and the pharmaceutical delivery modality may be disposed inside or outside of the case. The bracket may be used to anchor the device to a bone near the site of the injury to be repaired. The device may be employed to repair other injuries where tension is appropriate, such as torn ligaments, tendons or muscles.

In certain aspects of the disclosure, the tensioning apparatus of may comprise a ratcheting mechanism, a constant force spring, a servo-motor mechanism, a regulator, or other compatible substitute. The tensioning device can provide tension to the targeted transected or injured nerve. The tension can be regulated. The tensioning device may be disposed entirely within the case, partially within the case, or entirely outside of the case.

In certain aspects of the disclosure, the suture or other means for connecting to a nerve stump may comprise standard surgical suture or other appropriate substitutes. The means for connecting the device to a nerve stump need not be limited to a suture or other string-like apparatus but may comprise any means appropriate for delivering tension to a nerve stump.

In certain aspects of the disclosure, the pharmaceutical or treatment delivery modality may include a programmable pump disposed within or without the case, liposomal encapsulated pharmaceutical beads, or biodegradable polymer matrices. Alternatively or additionally, the pharmaceutical or treatment delivery modality may include means for stimulating the injured area physically including electrostimulation, temperature modulation, or delivery of light or vibration. The pharmaceutical or treatment delivery modality is intended to deliver pharmaceuticals or other treatments appropriate for improving the healing time of the injured tissue.

In certain aspects of the disclosure, the bracket may be mounted to a surface of the case for attaching the device to a bone or other appropriate attachment point. The bracket may be oriented in any configuration appropriate for ensuring that tension is delivered by the device in a manner conducive to healing the targeted tissue. The bracket may have screw holes or other means for attaching the device to the attachment point.

In certain aspects of the disclosure, the case may be contiguous with the bracket or may be a separate structure. The case may provide a complete or partial housing for the tensioning device and/or the pharmaceutical or treatment delivery modality or may be merely a conduit through which the suture or other structure passes in order to appropriately guide said suture or other structure.

In certain aspects of the disclosure, a tube of silicone or comparable material can be utilized, one end of which being sutured to capture the distal end of a peripheral nerve. The distal end of the severed peripheral nerve may be disposed inside of the tube structure and sutured to the inner or outer surface of said tube structure. A further tensioning device may be applied to provide variable tension controlled by a care provider to the tube to provide stretching stimulation to the severed peripheral nerve.

In certain aspects of the disclosure, the tube structure may be anchored to a bone by an anchoring device disposed proximally to the tube structure such that the anchoring device provides a directing means to bend the tube structure so that the tube is directed down the length of the anchoring device, then by way of the directing means, along the length of the bone such that the tube structure forms an angle between 20 and 160 degrees at the directing means. In an example embodiment the directing means may be a roller or other device serving a similar function.

In certain aspects of the disclosure, the tube structure may be arranged so as to deliver pharmaceuticals such as growth factors, biologics, anesthetics, or other compounds to the distal end of the severed peripheral nerve. The pharmaceuticals may be delivered by means of a drip or a device controlled flow.

In certain aspects of the disclosure, the tube structure may be tensioned by an external tensioning device such that a care provider can adjust the tension provided by the tube structure to the distal end of the severed peripheral nerve. The tensioning device may be located outside of the body of the patient and may be disposed on the anchoring device. Alternatively, the tensioning device may form a separate device from the anchoring device.

In certain aspects of the disclosure, the distal end or ends of the anchoring device may be disposed in the bone of a patient. The anchoring device may comprise a single anchor disposed into the bone of the patient or multiple anchors. Alternatively, multiple anchoring devices of various size and dimension may be used as appropriate to control or regulate the tension and disposition of the tube structure.

The foregoing discussion about tissue distraction for regenerative medicine and distraction neurogenesis is for illustrative purpose and provides disclosure without suggesting or causing limitation. Various aspects of the present disclosure may be more clearly understood and appreciated from a review of the following text and by reference to the associated drawings and the claims that follow. Other aspects, systems, methods, features, advantages, and objects of the present disclosure will become apparent to those with skill in the art upon examination of the following drawings and text. It is intended that all such aspects, systems, methods, features, advantages, and objects are to be included within this description and covered by this paper and by the appended claims.

While this disclosure provides certain specific embodiments, the technology is not limited to those embodiments. A person of ordinary skill in the art will appreciate from the description herein that modifications can be made to the described embodiments and therefore that the specification is broader in scope than the described embodiments. All examples are therefore non-limiting.

BRIEF DESCRIPTION OF THE FIGURES

The following drawings form part of the present specification and are included to further demonstrate certain aspects of the disclosure.

FIGS. 3A, 3B, 3C, and 3D are illustrations of certain elements of the regeneration system in accordance with some example embodiments of the disclosure.

Figure 1A:
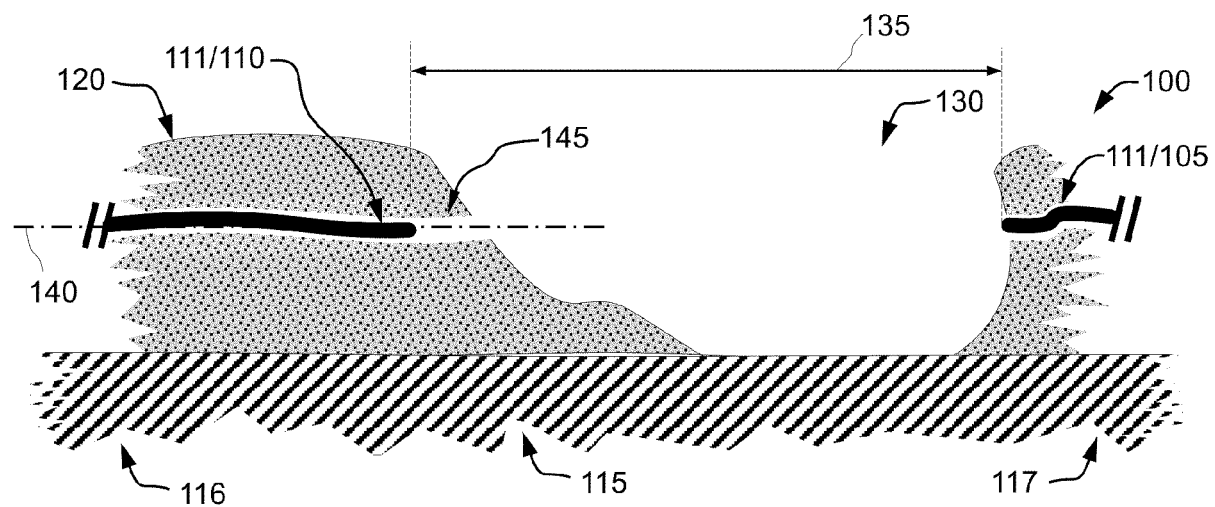
FIG. 1A is an illustration of a transected nerve and associated treatment site, distal nerve end, proximal nerve end, bone, soft tissue and associated nerve gap in accordance with some example embodiments of the disclosure.

Many aspects of the disclosure can be better understood with reference to these figures in combination with the description of specific embodiments presented herein. The elements and features shown in the figures are not necessarily to scale, emphasis being placed upon clearly illustrating the principles of example embodiments of the disclosure. Moreover, certain dimensions may be exaggerated to help visually convey such principles. In the figures, common reference numerals often designate like or corresponding, but not necessarily identical, elements throughout the several views.

DETAILED DESCRIPTION OF EXAMPLE EMBODIMENTS

Detailed descriptions of one or more embodiments are provided herein. It is to be understood, however, that the present technology may be embodied in various forms. Therefore, specific details disclosed herein are not to be interpreted as limiting, but rather as a basis for the claims and as a representative basis for teaching one skilled in the art to practice a variety of embodiments in any appropriate manner.

Those of ordinary skill in the art having benefit of this disclosure will be able, without undue experimentation, to combine compatible elements and features that are described in detail at various places in this written description, which includes text and illustrations. That is, the figures and specification are organized to facilitate practicing numerous combinations, such as by combining elements of one illustrated or textually-described embodiment with other elements of one or more other illustrated or textually-described embodiments.

Whenever the phrases "for example", "such as", "including", and the like are used herein, the phrase "and without limitation" is understood to follow unless explicitly stated otherwise. Similarly, "an example," "exemplary," and the like are understood to be non-limiting.

The terms "comprising" and "including" and "having" and "involving" (and similarly "comprises", "includes", "has," and "involves") and the like are used interchangeably and have the same meaning. Specifically, each of the terms is defined consistent with the common United States patent law definition of "comprising" and is therefore interpreted to be an open term meaning "at least the following" and is also interpreted not to exclude additional features, limitations, aspects, etc. Thus, for example, "a process involving steps a, b, and c" means that the process includes at least steps a, b, and c. As another example, when a first device comprises a second device, the first device may include the second device or the second device may include the first device.

Whenever the terms "a" or "an" are used, "one or more" is understood, unless such interpretation is nonsensical in context.

The term "couple," as may be used herein, generally refers to joining, connecting, or associating something with something else.

As one of ordinary skill in the art will appreciate, the term "operably coupled," as may be used herein, encompasses direct coupling and indirect coupling via another, intervening component, element, circuit, or module; moreover, a first component may be operably coupled to a second component when the first component comprises the second component.

As one of ordinary skill in the art will appreciate, the term "substantially" or "approximately," as may be used herein, provides an industry-accepted tolerance to its corresponding term. Such an industry-accepted tolerance ranges from less than one percent to twenty percent and corresponds to, but is not limited to, component values, process variations, and manufacturing tolerance.

As further disclosed below, some embodiments of a system for tissue regeneration can comprise one or more of a drive, a retractor, a regulator, a controller, a coupler, a reel, a line, and an energy storage device, not necessarily as distinct elements. Further, these terms may have overlapping scope. For example, a spring-loaded reel can comprise a retractor, a regulator, a controller, and an energy storage device. Similarly, a method or process for tissue regeneration can comprise one or more of driving, retracting, regulating, controlling, coupling, reeling, and storing energy, not necessarily as distinct actions. Further, these terms may have overlapping scope.

Turning now to the figures, the technology will be further described with reference to example illustrated embodiments. FIGS. 1A-1F illustrate an example embodiment of a system 150 for regeneration in an example application of nerve regeneration. The system 150 may be employed to regenerate severed or damaged nerves in a human or other animal or may be used in other contexts wherein tension may be advantageous to improve regeneration of damaged tissue other than nerve tissue, such as severed ligaments, tendons or muscles. FIGS. 1A-1F will now be discussed in detail.

FIG. 1A is an illustration of an example treatment site 100 in which the example system 150 may be employed. In the illustrated example, an injury 130 resulted in a transection of a nerve 111, creating a distal nerve end 105 and a proximal nerve end 110 separated by a nerve gap 135, which is disposed between the proximal and distal nerve ends 105, 110. As discussed above, in various embodiments, the nerve injury 130 may have resulted from trauma, combat injury, cancer, congenital condition, lesion, bacterial or fungal infection, or some other malady or issue. In some embodiments, the distal and proximal nerve ends 105, 110 have been surgically produced, for example by surgical removal of a section of a nerve 111 that a medical practitioner has deemed to be nonviable.

As illustrated, the nerve 111 has a longitudinal axis 140, which in the example embodiment of FIG. 1A extends from the proximal nerve end 110 across the nerve gap 135 towards the distal nerve end 105. The nerve 111 extends through soft tissue 120 in a nerve channel 145. The nerve 111 extends along bone 115 with a proximal portion of the bone 116 corresponding to the proximal nerve end 110 and a distal portion of the bone 117 corresponding to the distal nerve end 105.

Figure 1B:
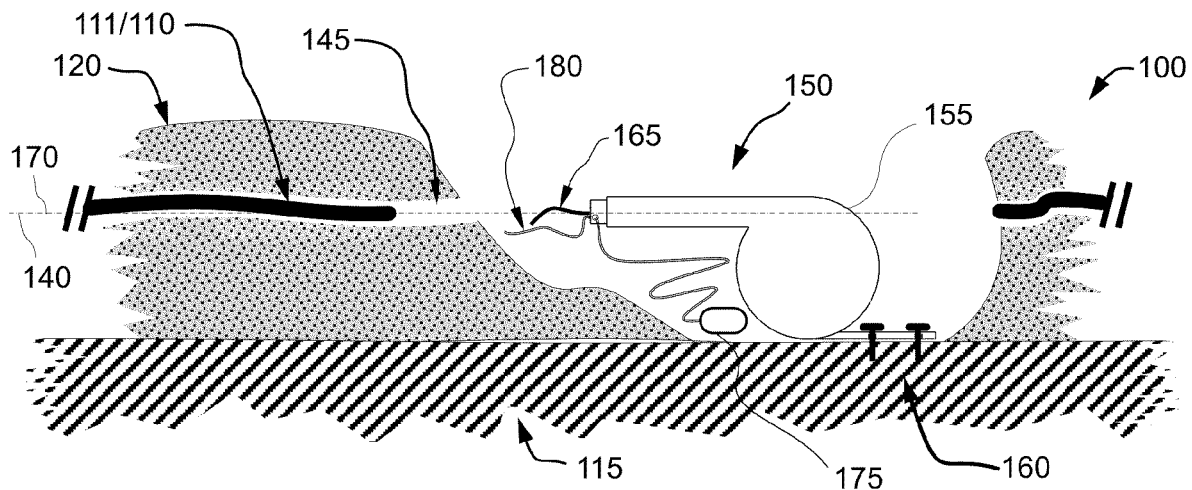
FIG. 1B is an illustration of an installation of a regeneration system in accordance with some example embodiments of the disclosure.

FIG. 1B is an illustration of an example installation of the system 150, as may be performed by a surgeon on a human patient, a nonhuman primate, zoo animal, pet, race horse, or another appropriate vertebrate or other animal. In the illustrated example of FIG. 1B, the system 150 comprises a distraction unit 155 with an associated line 165 and a pump system 175 with an associated tube 180, which will be discussed in detail with reference to subsequent figures.

FIG. 1B particularly illustrates an initial phase of installation, in which the distraction unit 155 has been anchored or fastened to the bone 115 with fasteners 160. The fasteners 160 may comprise screws, staples, adhesives, cements, or other appropriate fastening means. In various embodiments, the line 165 may comprise monofilament, thread, or suture material for connecting the distraction unit 155 to the proximal nerve end 110 in order to generate tension along the distraction axis 170, which extends alongside and approximately aligns with the longitudinal axis 140 of the nerve 111. In some example embodiments, the line 165 comprises nylon or fluoropolymer material.

In one example embodiment, the line 165 comprises a segment of elastic material (or may be elastic along essentially its entire length), such as a tube or strand of medical-grade silicone elastomer. In one example embodiment, such an elastomeric composition can stretch in accordance with applied tension and may absorb or damp tension spikes associated with patient movement.

In one example embodiment (not illustrated), the surgeon sutures one end of an elastic line to the proximal nerve end 110, stretches the elastic line, and then sutures the other end to a distal portion of bone 117 or to the distal nerve end 105. The stretched elastic line can thus apply sustained distractive force to one or both nerve ends 105, 110 to stimulate growth.

As further discussed below with reference to subsequent figures, in various example embodiments, the distraction unit 155 may comprise a constant force spring or a servo-motor mechanism. A servo-motor mechanism may be wirelessly connected to a host controller for regulation or modification of torque settings, such as to tune or maintain an amount of tension placed on the proximal nerve end 110.

The example pump system 175 comprises a reservoir (not illustrated) for one or more pharmaceutical agents or other treatment modalities, which the pump system 175 pumps through the tube 180 to the proximal nerve end 110. In some embodiments, the pump system 175 comprises two or more reservoirs for storing two or more agents along with a capability for drawing the agents selectively from each reservoir, for example to create an on-demand blend that may be adjusted during treatment.

In some example embodiments, the pump system 175, or a second pump (not illustrated), may connect to a second tube (not illustrated) for delivery of pharmaceutical agents or other treatment modalities to the distal nerve end 105. In various embodiments, the pump system 170 and associated tube 180 can deliver anesthetics, nutrients, growth factors, pharmaceuticals recognized as encouraging nerve growth, oxygenated fluid, gaseous oxygen, or combinations of such materials or other substances that promote nerve regeneration. In some example embodiments, the pump system 175 and associated tube 180 deliver one or more materials described in the above Background section that are recognized as supporting nerve regeneration.

It is to be understood by one having ordinary skill in the art that the device described herein may be used for veterinary applications and for research as well as for human patients in trauma and other medical conditions as discussed above. In some example embodiments, the pump system 175 may comprise a micro infusion pump commercially available from Primetech Corporation of Tokyo, Japan under the registered trade name of "IPRECIO," such as the products bearing the model numbers "SMP-310" or "SMP-200." Pump system 175 may comprise a microcontroller or microprocessor and further be capable of wireless communication with a host controller for modification of dosage and flow rate. In some example embodiments, the pump system 175 comprises an automatic feedback loop that regulates delivery of one or more pharmaceuticals according to detected nerve growth or other sensed physiological parameters. For example, as the proximal nerve end 110 lengthens (or when a threshold length is achieved), the controller may automatically adjust pharmaceutical delivery parameters, such as ceasing, reducing, or increasing delivery rate or switching from one pharmaceutical agent to another or changing relative concentrations of pharmaceutical agents in a blended composition.

As illustrated, the pump system 175 may be disposed in or adjacent to the injury site 100 or above the injury site 100. In the illustrated embodiment, the pump system 170 is implanted; in some other embodiments, the pump system 175 is disposed external to the patient, with the tube 180 extending into the treatment site 100. In various embodiments, the pump system 175 may be placed subcutaneously or in-line with the system 150 or the distraction unit 155. Subcutaneous placement of the pump system 175 can facilitate convenient replacement or refilling of the pump reservoir. In some embodiments, the tube 180 may comprise an elastomeric material (for example medical-grade silicone) to reduce any drag associated with retraction of proximal nerve end 110.

In some example embodiments, the tube 180 further comprises an optical waveguide for delivering visible, infrared, or ultraviolet light to stimulate growth or otherwise provide benefit. For example, an optical fiber can be embedded in a wall of the tube 180 or may extend alongside the tube 180. A laser light source or light emitting diode coupled to the optical fiber may be included in pump system 175, for example.

The tube 180 may further comprise electrical lines (embedded or running alongside) and electrodes for delivering electrical stimulation to the proximal nerve end 110 to stimulate growth, maintain activity in the nerve 111, or otherwise provide benefit. The electrodes may additionally or alternatively be connected to the distal nerve end 105. An associated electrical source may be included in pump 175. Such electrical lines may further provide electricity for a transducer (not illustrated) positioned adjacent the proximal nerve end 110 (or the distal nerve end 105). The transducer can convert the electricity into a form of energy having a potential to encourage nerve growth and/or suppress pain, for example comprising a piezoelectric element that vibrates or emits waves.

Figure 1C:
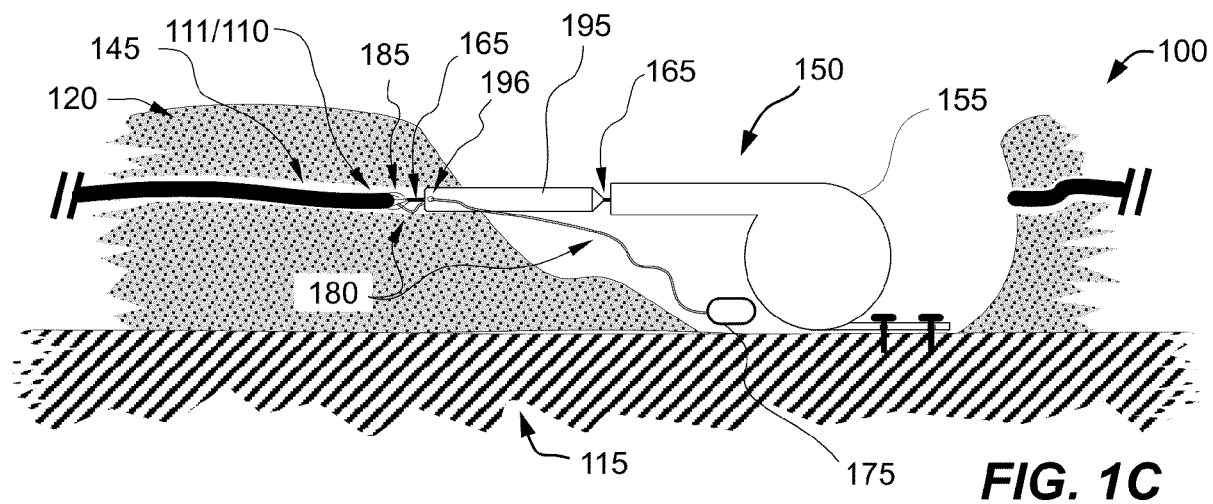
FIG. 1C is a further illustration of the installation of the regeneration system in accordance with some example embodiments of the disclosure.
Figure 1D:
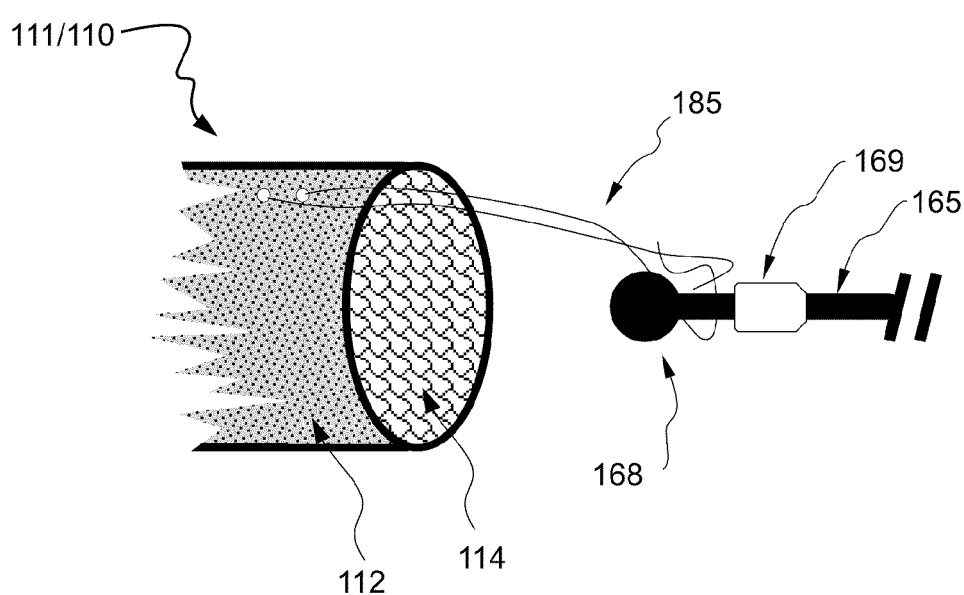
FIG. 1D is a further illustration of the installation of the generation system focused on the proximal nerve end of the transected nerve in accordance with some example embodiments of the disclosure.

FIGS. 1C and 1D are further illustrations of the example installation of the system 150, particularly illustrating a second phase of installation in which the line 165 is attached to the proximal nerve end 110. As illustrated by FIG. 1C, the line 165 and a traveling nerve channel stent 195 have been extended from the distraction unit 155, which is anchored to bone 115 as discussed above. A surgeon may pull the line 165 and traveling nerve channel stent 195 out of the distraction unit 155 and use a hemostat or clip to relieve retractive force during the installation procedure, for example.

As illustrated in FIG. 1C, the traveling nerve channel stent 195 helps keep the nerve channel 145 open so that the proximal nerve end can grow without undue occlusion or interference. In some example embodiments, the traveling nerve channel stent 195 can comprise a structure of sufficient mechanical integrity to maintain a nerve channel 145. The traveling nerve channel stent 195 can comprise medical-grade fluoropolymer, stainless steel, titanium, or a mesh or wire frame, for example. In some example embodiments, the traveling nerve channel stent 195 can comprise a membrane, a porous member, or a structure that is permeable to gas, liquids, or substances that support nerve regeneration. The traveling nerve channel stent 195 can comprise one or more biopolymers, a mesh, a woven fabric, or a non-woven fabric, to mention some representative embodiments. In some example embodiments, the traveling nerve channel stent 195 can comprise one or more pharmaceutical agents that are eluted or otherwise released to the nerve 111 or otherwise to the treatment site 100. In some example embodiments, the traveling nerve channel stent 195 can comprise a commercially available nerve guidance conduit or artificial nerve conduit.

As discussed below, in some embodiments, the traveling nerve channel stent 195 travels with nerve growth to keep the nerve channel 145 open. In some example embodiments, the traveling nerve channel stent 195 may be viewed as a pilot. In some example embodiments, the traveling nerve channel stent 195 is replaced with a nerve guidance conduit or artificial nerve conduit or a stent that is permanently implanted in a static position (so that it does not travel with nerve growth). In such an embodiment, the line 165 can extend through the bore 197 (first labeled at FIGS. 1E and 1F) of the conduit or stent and apply force to the proximal nerve end 110 that effectively pulls the nerve end 110 into or towards the bore 197.

As illustrated, the tube 180 feeds through a hole 196 in the traveling nerve channel stent 195 and extends along with the line 165. Thus tube 180 passes through hole 196 such that the delivery end of the tube 180 is disposed proximate to proximal nerve end 110.

FIG. 1D illustrates the installation focused on the proximal nerve end 110 of the transected nerve 111. With the line 165, the tube 180, and traveling nerve channel stent 195 extended, the surgeon can attach the line 165 to the distal nerve end 110 as illustrated in the detail view of FIG. 1D. Line 165 is sutured to the proximal nerve end 110 with sutures 185, which attach to a knot 168 in the line 165.

Each suture 185 is disposed in the myelin sheath 112 of axon 114 as shown in FIG. 1D. The surgeon may create an array of suture attachments that collectively circumscribe the myelin sheath 112, for example on intervals of 60 degrees so that six sutures attach the line 165 to the myelin sheath 112. The number of suture attachments may be selected in practice according to the size or location of the nerve 111, the level of retractive force prescribed, the age of the patient, and/or other factors deemed relevant.

A crimp-on imaging marker 169 is attached to the line 165 as a location aid. In an example embodiment, the crimp-on imaging marker 169 comprises a bead of metal or other material that is conducive to location using ultrasound, x-rays, or other imaging modality. The imaging marker 169 supports assessing nerve growth using non-invasive imaging, since the marker 169 moves as the proximal nerve end 110 undergoes distraction neurogenesis as discussed below.

Figure 1E:
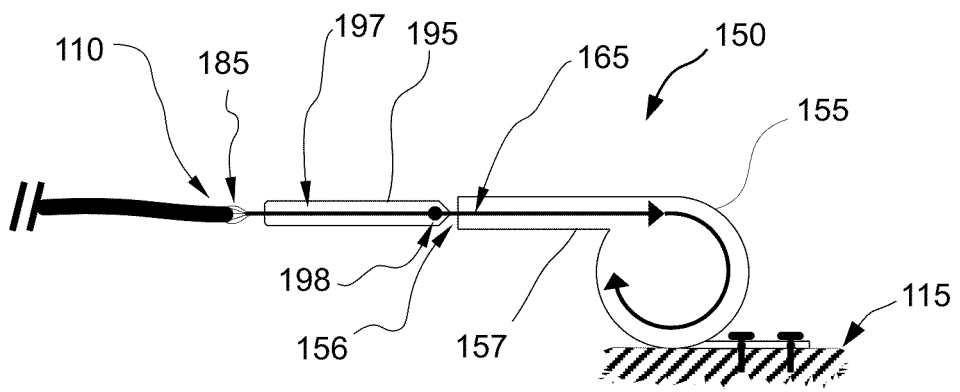
FIG. 1E is an illustration of the regeneration system in the treatment site after installation in accordance with some example embodiments of the disclosure.
Figure 1F:
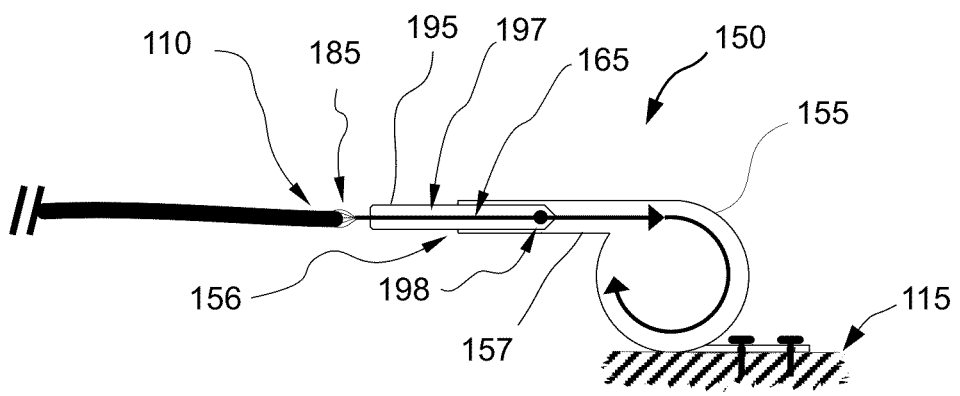
FIG. 1F is an illustration of the regeneration system after at least a portion of a treatment period has passed, the nerve segment having been regenerated in accordance with some example embodiments of the disclosure.

FIGS. 1E and 1F are illustrations of the system 150 after installation at the injury site 100 at the start of treatment and at the completion of treatment respectively. FIGS. 1E and 1F respectively illustrate the traveling nerve channel stent 195 extracted from and inserted in an aperture 156 in an extension 157 of the distraction unit 155.

As discussed above, in the illustrated embodiment, the system 150 is attached to bone 115, and the distraction unit 155 is attached to the proximal nerve end 110 via the line 165 with sutures 185. The traveling nerve channel stent 195 is depicted transparent in FIGS. 1E and 1F to visually convey how the line 165 can extend through the bore 197 of the traveling nerve channel stent 195. The transparent depiction further illustrates how a crimp-on retention bead 198 is captured to provide independent proximal motion of the traveling nerve channel stent 195 during installation and to cause joint motion in the distal direction after installation. The cross-sectional view of FIG. 5 (discussed below) illustrates further details about how travelling nerve channel stent 195 is attached to line 165 with crimp-on retention bead 198 in the illustrated example.

In operation, as the proximal nerve end 110 is pulled towards the distraction unit 155, it is guided by the travelling nerve channel stent 195 which can keep the nerve channel 145 open during the period of treatment. Example embodiments and operations of the distraction unit 155 will be further described below with reference to subsequent figures.

Figure 2:
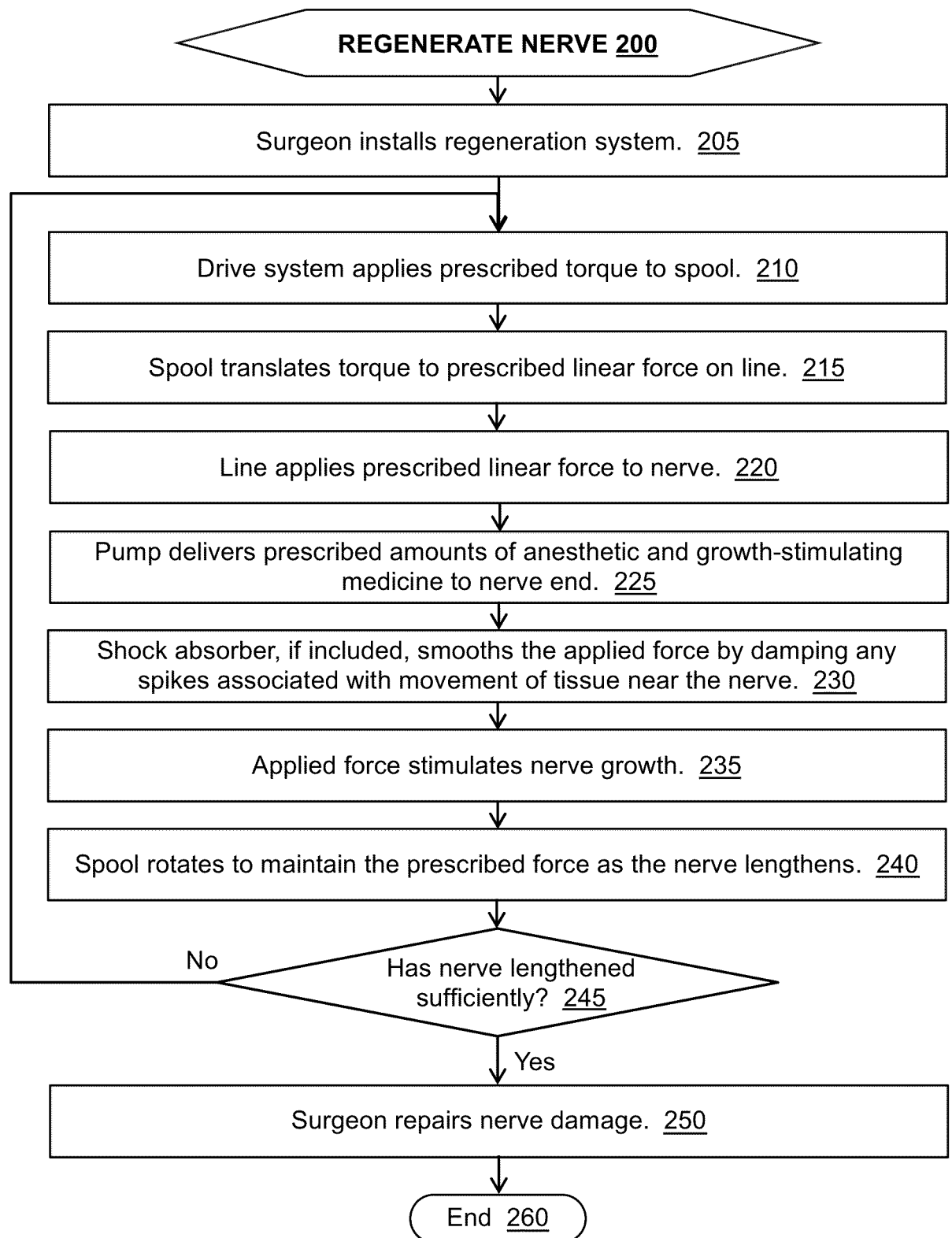
FIG. 2 is a flowchart describing a method of action of the regeneration system in accordance with some example embodiments of the disclosure.

Turning now to FIG. 2, this figure illustrates a flowchart disclosing an example process or method 200 of action of the system 150. In a representative embodiment, a care provider (for example a surgeon, physician, veterinarian or other appropriate medical practitioner) determines that treatment of an injury to a peripheral nerve in a limb (or appropriate nerve other appropriate body part) would be improved by regeneration of a severed nerve and elects to initiate the process 200.

Certain steps or actions of the process 200, as well as of the other processes and methods disclosed or taught herein, may naturally need to precede other steps or actions to achieve desirable functionality. However, the disclosure is not limited to the order of the steps or actions described if reordering or resequencing does not adversely alter functionality to the extent of rendering the technology inoperable or nonsensical. Accordingly, it is recognized that some steps or actions may be performed before or after others or in parallel with others without departing from the scope and spirit of the disclosure.

At block 205 of process 200, a surgeon installs the system 150. A care provider (for example comprising the surgeon, another profession, or a team) can determine an appropriate torque to effectively regenerate the nerve 111 and may select hardware or tension settings according to patient size and body part. For example, a particular size of traveling nerve channel stent 195 can be selected according to nerve diameter and physiology. In some example embodiments, tension in a range of approximately a tenth of an ounce of force (approximately 0.03 N) to approximately ten ounces of force (approximately 3 N) may be selected. Larger nerves or larger subjects may generally warrant larger force applications. In one example embodiment, applied tension is in a range of approximately one-half ounce (approximately 0.1 N) to approximately three ounces (approximately 0.8 N) for a peripheral nerve in an animal weighing approximately 150 pounds (approximately 68 kg).

At block 210, the distraction unit 155 applies the specified torque value to a reel or servo-motor mechanism within the distraction unit 155. Subsequent figures, discussed below, illustrate example embodiments of these elements.

At block 215, the reel or servo-motor mechanism translates the torque to linear force or tension on the line 165. Subsequent figures, discussed below, illustrate example embodiments of these elements.

At block 220, the line 165 applies the linear force to the proximal nerve end 110.

At block 225, the pump system 175 delivers medication to the proximal nerve end 110.

Figure 9:
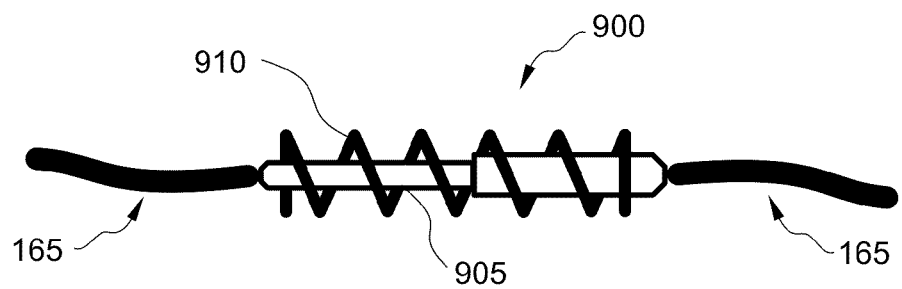
FIG. 9 is an illustration of certain elements of the regeneration system in accordance with some example embodiments of the disclosure.

At block 230, a shock absorber may be included to smooth the applied force by damping spikes associated with movement of tissue near the nerve 111, for example as the patient moves or is moved. FIG. 9, discussed below, illustrates an example embodiment of a shock absorber.

At block 235, the applied force stimulates nerve growth.

At block 240, the reel or servo-motor mechanism maintains the prescribed force as the nerve 111 lengthens. The applied force can accordingly be regulated. The applied force can alternatively be regulated by following a predetermined trajectory or path, for example decreasing or increasing in a predetermined or selected manner as the nerve 111 lengthens.

At decision block 245 an inquiry is made as to whether the treatment has produced sufficient nerve regeneration. If the decision is negative, then process 200 loops back to block 210 and blocks 210 - 240 iterate until sufficient regeneration has been achieved. In some example embodiments, the decision is automatic, such as by software stored in nonvolatile memory of the system 150 and executed by a controller of the system 150. In some example embodiments, once the system 150 has determined that nerve growth is sufficient, the system 150 emits a wireless indicator signal for reception by a detector located outside the patient, thereby notifying of completion (or of intermediate progress).

In some example embodiments, the care provider determines when the treatment has resulted in sufficient nerve regeneration. In some example embodiments, the care provider uses non-invasive imaging to determine location of the imaging marker 169 which correlates to nerve growth.

At block 250, once sufficient regeneration has occurred, the surgeon rejoins the distal and proximal nerve endings 105, 110.

Once the surgeon has joined the nerve ends 105, 100, process 200 ends at block 260.

Referring now to FIGS. 3A-D, these figures illustrate orthonormal views of the distraction unit 155 along with the traveling nerve channel stent 155, both as example embodiments thereof. For viewing clarity, the drive mechanism and internal cavity of the distraction unit 155 are not depicted in these views, but rather are illustrated in FIG. 6. A shoulder 300 (illustrated in FIG. 5 in detail) provides a mechanical stop that prevents the distraction unit 155 from retracting the traveling nerve channel stent 195 into the internal workings of the distraction unit 155.

Figure 4:
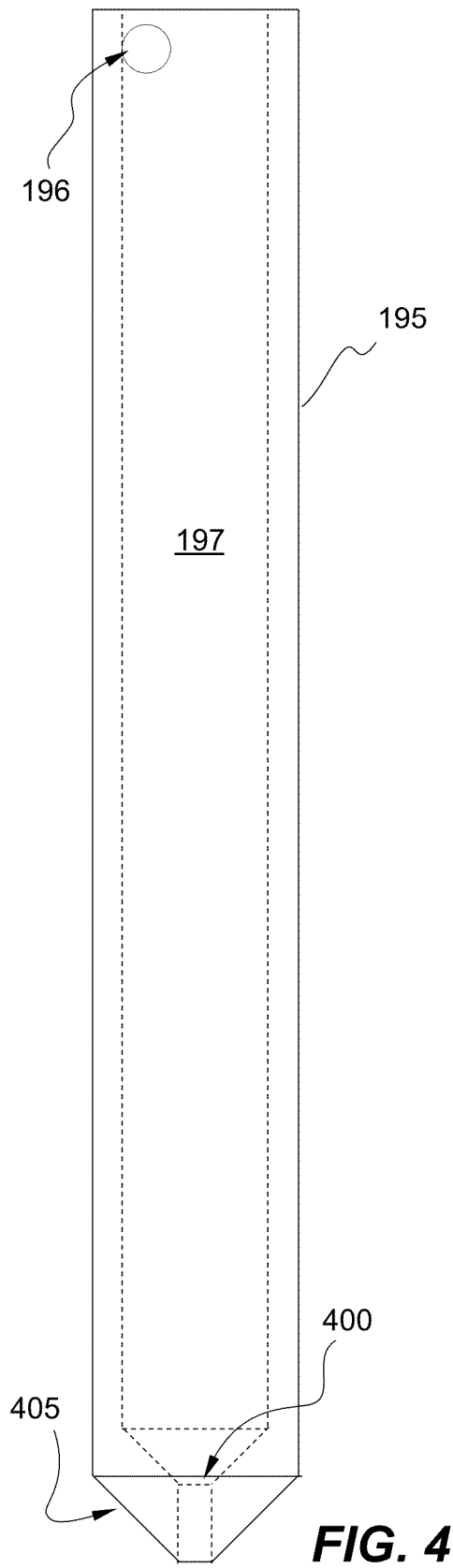
FIG. 4 is an illustration of certain elements of the regeneration system in accordance with some example embodiments of the disclosure.

Referring now to FIG. 4, this figure provides a view of an example embodiment of the travelling nerve channel stent 195. A hole 400 provides passage for the line 165 into and through the bore 197 of the travelling nerve channel stent 195. A tapered end 405 of the travelling nerve channel stent 195 seats against the shoulder 300 and further can provide a nose cone to facilitate moving through soft tissue with reduced drag. The tapered end 405 can further facilitate reception by the aperture 156 in the extension 157 of the distraction unit 155.

Figure 5:
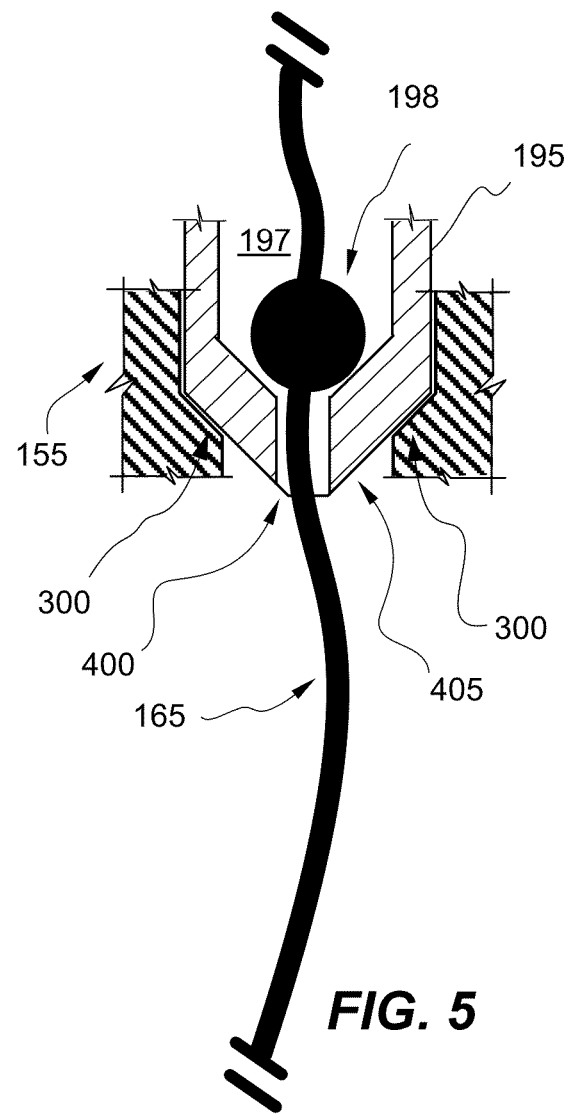
FIG. 5 is an illustration of certain elements of the regeneration system in accordance with some example embodiments of the disclosure.
Figure 6:
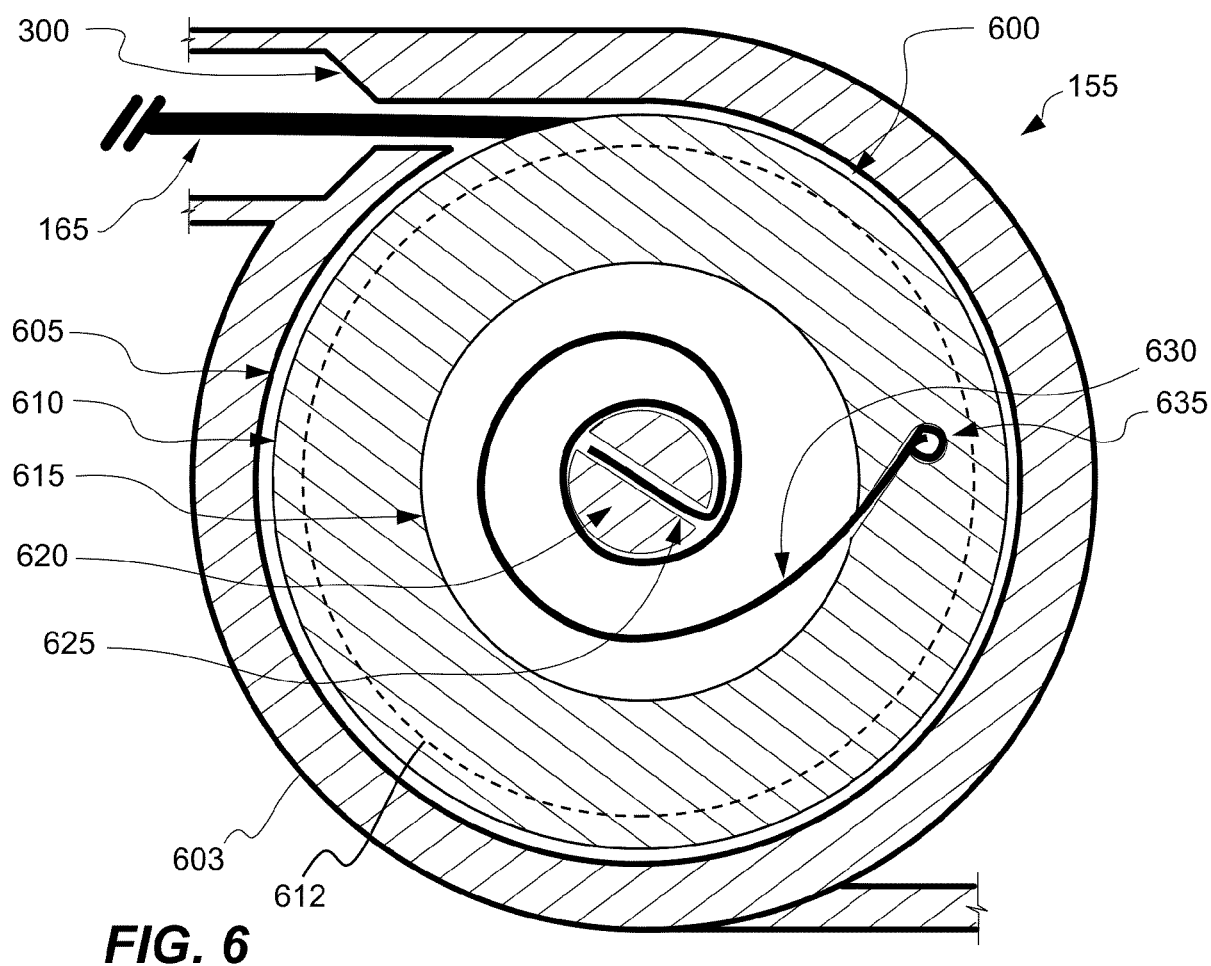
FIG. 6 is an illustration of certain elements of the regeneration system in accordance with some example embodiments of the disclosure.

Referring now to FIG. 5, this figure is a detail view of the line 165 passing through hole 400 in the tapered end 405 of traveling nerve channel stent 195. The tapered end 405 seats against shoulder 300. A crimp-on retention bead 198 prevents the line 165 from being draw back into the distraction unit 155 beyond a pre-determined distance.

Referring now to FIG. 6, this figure illustrates a cross sectional view of an example embodiment of the distraction unit 155. In operation, the line 165 is retracted into the housing 603 of the distraction unit 155, through shoulder 300, by a drive system 600 that rotates a reel 610. The reel 610 comprises a cylindrical winding surface 612 about which the line 165 winds as the drive system 600 rotates the reel 610.

The reel 610 is disposed in a cavity 605 of the housing 603, which can be formed of medical-grade stainless steel, titanium, or other biocompatible material suitable for implanting. As illustrated, the housing cavity 605 is sized to match the reel 610, so that the reel 610 is located coaxially with respect to a housing post 620 and has clearance to rotate freely. For example, the housing cavity 605 can have a diameter that is oversized relative to the reel 610, for example to provide a radial clearance in a range of 0.1 to 2.0 millimeters or another appropriate value as may be varied for different sizes, forces, applications, and construction materials.

In the illustrated example, the drive system 600 comprises a spring 630 that is coaxially disposed with respect to the reel 610 and the housing post 620. As illustrated, the spring 630 is disposed in a coiled state a cavity 615 of the reel 610. The spring 630 is held at one end by a spring retention slot 625 in the housing post 620 and at the other by a spring retention aperture 635 disposed within the reel 610. In some embodiments, a rotary damper or other damper (not illustrated in FIG. 6) may be included to smooth spikes in force associated with limb movement.

In various embodiments, the spring 630 may have more or fewer coils than illustrated. The number of coils can be selected according to whether or how much the force delivered is to be constant or is to vary over the length of travel, and/or further by the overall length of travel. In some embodiments, the retractive force varies linearly over the length of travel. In some embodiments, the retractive force varies less than 2, 5, 10, or 15 percent over the length of travel. In the illustrated embodiment, the spring 630 comprises a coiled strip of metal (such as spring-tempered stainless steel); in some other embodiments, the spring 630 comprises a length of spring wire that may be coiled. In an example alternative embodiment, a silicone elastomeric member supplies rotational force to the reel 610.

In some example embodiments (without limitation), the spring 630 can comprise one or more of a constant force spring, a constant torque spring, a power spring, a spiral spring, a clock spring, a strip spring, or a wire spring, as such terms are typically applied in industry and as understood by those of skill in the art having benefit of the present disclosure. The preceding sentence is not intended to imply that the terms may have overlapping scope.

In some example embodiments, the drive system 600 can comprise a spring or spring drive commercially available from the Spiroflex division of KERN-LIEBERS Ltd. of Schramberg, Germany. In some example embodiments, the drive system 600 can comprise a spring or spring drive commercially available from Vulcan Spring of Telford, PA, USA under the trade identifier "CONFORCE" for constant force springs or the trade identifier "CONTORQUE" for constant torque springs. In some example embodiments, the drive system 600 can comprise a spring drive system commercially available from the West Coast Corporation of Ontario, California, USA, such as the drive system in the consumer product that the company markets as "MINI-BAK RETRACTABLE BADGE HOLDER, SKU 0055-005" which is available in a choice of two or four ounces of specified retraction force. In some example embodiments, the drive system 600 can comprise a spring or spring drive commercially available from the Hunter Spring division of AMETEK. Inc. in Horsham, PA, USA, such as the spring motor assemblies marketed under the trade identifier "NEG'ATOR" and designated as part number ML-1448.

In some example embodiments, the spring drive system 600 comprises a servo-motor drive system, which will be further discussed below with reference to FIG. 11.

Figure 7A:
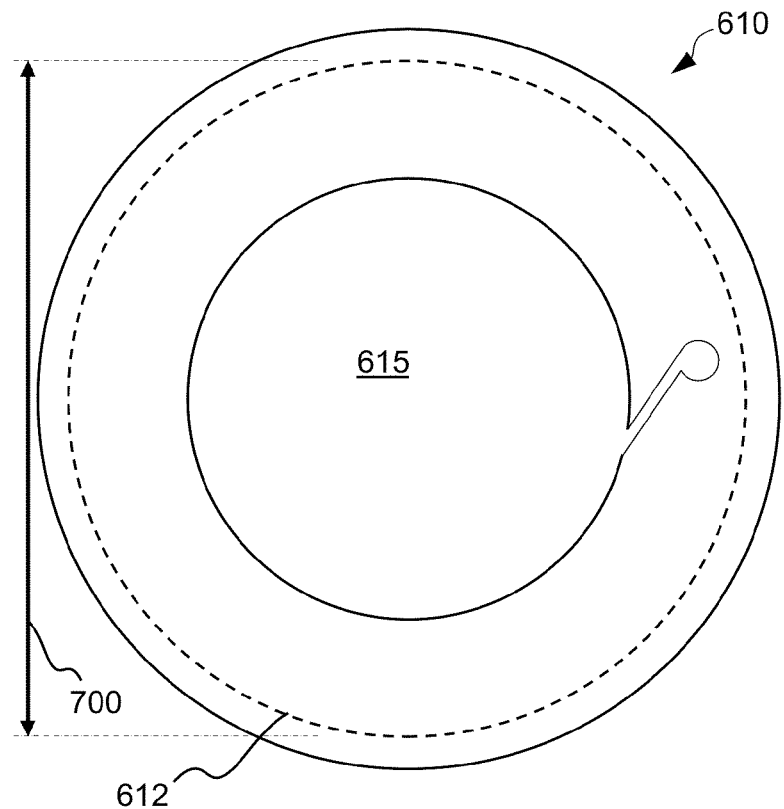
FIGS. 7A and 7B are illustrations of certain elements of the regeneration system in accordance with some example embodiments of the disclosure.
Figure 7B:
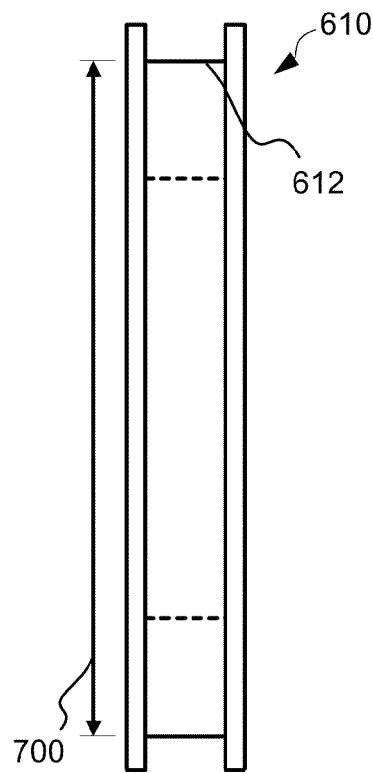

Referring now to FIG. 7A and B, these figures illustrate orthonormal views of an example embodiment of the reel 610. In some example embodiments, the reel 610 is composed of stainless steel or an appropriate polymer such a fluoropolymer, nylon, or acetal resin. The diameter 700 of the cylindrical winding surface 612 correlates with the tension that a particular drive system 600 applies to the line 165 in the configuration illustrated at FIG. 6. Increasing the diameter 700 decreases line tension, while decreasing the diameter 700 increases line tension. Accordingly, reel diameter 700 can be selected to achieve a selected line tension.

Figure 8:
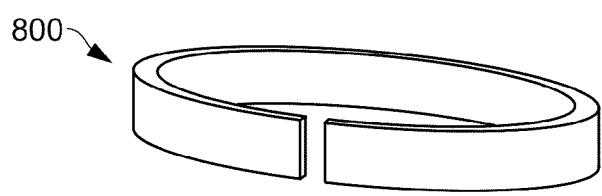
FIG. 8 is an illustration of certain elements of the regeneration system in accordance with some example embodiments of the disclosure.

Referring now to FIG. 8, this figure illustrates a perspective view of a spacer 800 for increasing the effective diameter 700 of the cylindrical winding surface 612 of the reel 610. In application, the spacer 800 can be snapped onto or otherwise disposed on the reel 610, over the cylindrical winding surface 612. This provides a capability to vary the diameter 700 of the cylindrical winding surface 612 and thus applied force. As an alternative to the spacer 800, the reel 610 can be partially filled with backing line to increase the diameter 700. Another alternative for achieving different forces (as may be beneficial for different applications) is to swap out springs with different force characteristics or to increase force by using multiple springs at the same time.

Referring now to FIG. 9, this figure is an illustration of a shock absorber 900 disposed on the line 165 as an example embodiment of a damper. The illustrated shock absorber 900 includes a dashpot 905 and a spring 910 for damping. The shock absorber 900 can relieve spikes in force associated with limb movement. In some example embodiments, the shock absorber 900 may positioned adjacent the proximal nerve end 110 or inside the traveling nerve channel stent 195. In some embodiments, a damper (such as a shock absorber, dashpot, or rotary damper) is included in the mechanisms of the drive system 600 inside the housing 603 of the distraction unit 155.

Figure 10B:
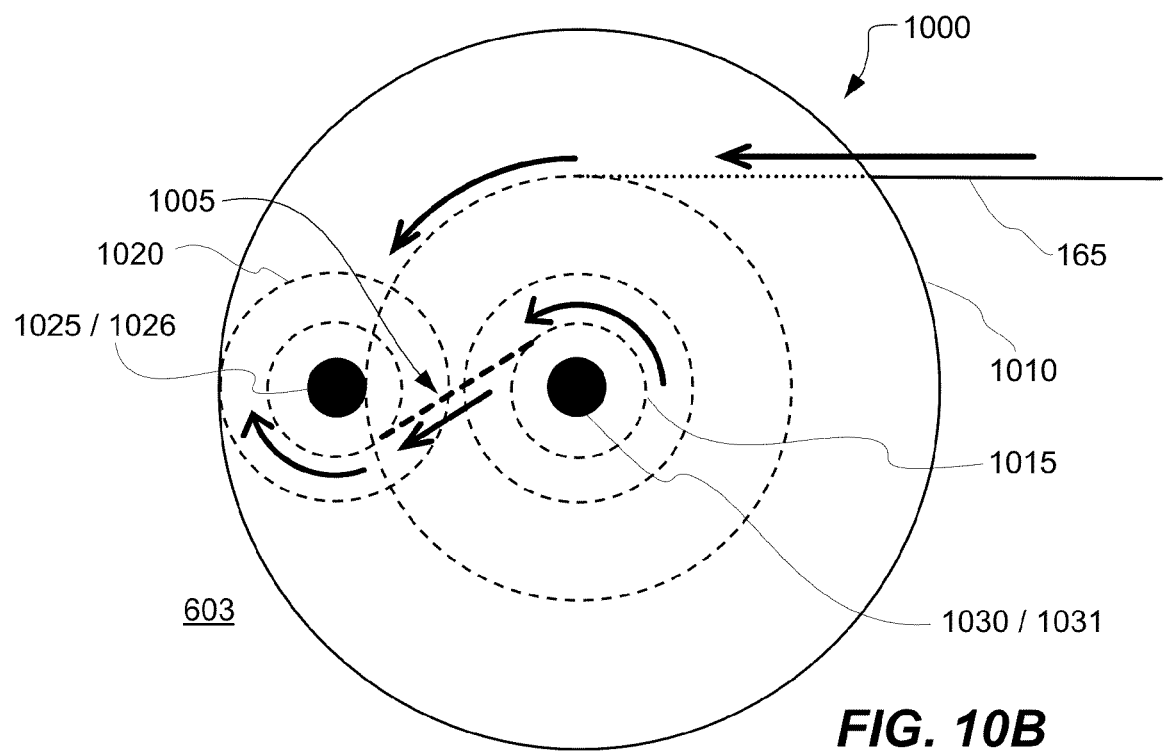
FIGS. 10A and 10B are illustrations of another regeneration system in accordance with some example embodiments of the disclosure.
Figure 10A:
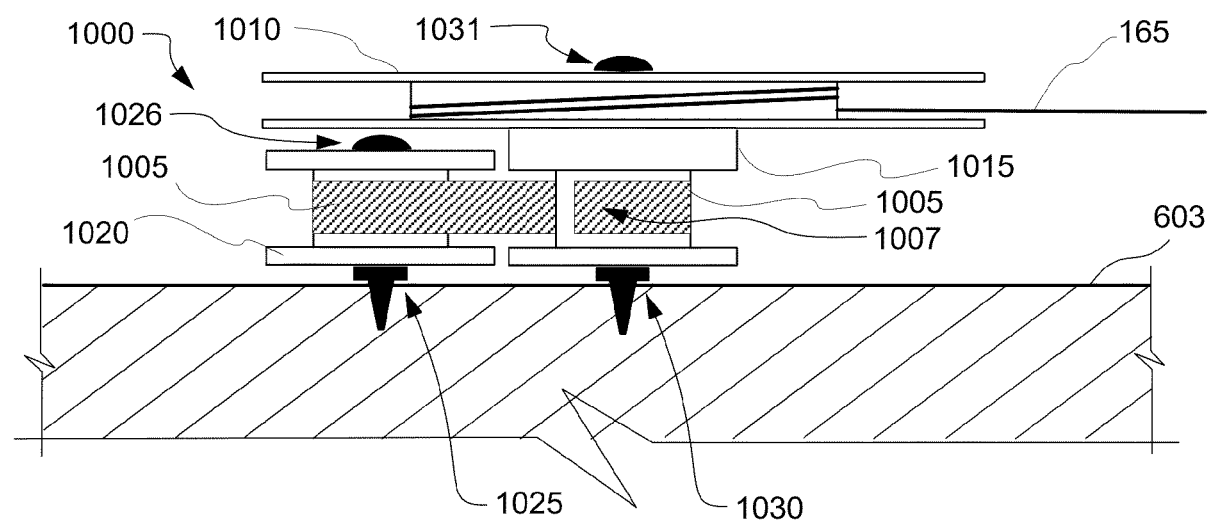

Turning now to FIG. 10A and B, another example embodiment is illustrated and will now be discussed. FIGS. 10A and 10B are illustrations of an example drive system 1000, with FIG. 10A illustrating an overhead view and FIG. 10B illustrating a side view. The drive system 1000 can be enclosed in a housing in accordance with the housing 603 illustrated in FIG. 6. For example, the drive system 1000 can be enclosed in a housing having the outward geometry of the illustrated housing 603 with an interior space configured to accommodate the drive system 1000. The drive system 1000 can be operated in accordance with the foregoing discussion. Accordingly, the drive system 1000 can provide retractive tension on the line 165. Additionally, the drive system 1000 can comprise one or more shock absorbers 900 (see FIG. 9 and accompanying discussion) or other appropriate damper.

As illustrated, the example drive system 1000 comprises two shafts 1025, 1030 that are mounted to the housing 603, for example via threads, press fit, weld, braze, epoxy, or other appropriate fastening means. The two shafts 1025, 1030 can be formed of stainless steel or other appropriate material.

A spring drum 1020 is mounted to and rotates freely about the shaft 1025, with a shaft head 1026 capturing the spring drum 1020 on the shaft 1025. In some embodiments, the shaft head 1026 is countersunk in a recess in the spring drum 1020, in which case the shaft head 1026 would be hidden in the view of FIG. 10A. Countersinking can provide a compact profile.

Another spring drum 1015 and a reel 1010 are mounted to and rotate freely in unison about the shaft 1030, with a shaft head 1031 capturing them on the shaft 1030. The shaft head 1031 can be countersunk in a recess in the reel 1010 as discussed in the immediately preceding paragraph. The spring drum 1015 and the reel 1010 can be formed out of a unitary piece of material (for example a piece of stainless steel) or otherwise connected to one another to provide unitary rotation.

In the illustrated embodiment, a constant force spring 1005 extends circumferentially around each of the spring drums 1015, 1020. That is, one end (hidden from view in FIGS. 10A and 10B) of the constant force spring 1005 wraps about the spring drum 1020, and the opposite end 1007 of the constant force spring 1005 wraps about and is attached to the spring drum 1015. While the spring end 1007 is illustrated in the view of FIG. 10A, in practice the end 1007 may be hidden from view by additional windings about the spring drum 1015. For example, the length of the constant force spring 1005 may be selected according to desired travel distance, with a margin of at least one additional wrap to avoid over-extension issues.

In operation, the constant force spring 1005 seeks to transition to a low-energy state whereby the windings transfer from the spring drum 1015 to the spring drum 1020. In other words, the constant force spring 1005 wants to release stored energy by unwinding from the spring drum 1015 and winding onto the spring drum 1020. As illustrated by the representative arrows overlaid upon the view of FIG. 10B, the constant force spring 1005 thus applies rotational force or torque to the spring drum 1015, which in turn applies rotational force or torque to the reel 1010, which in turn applies linear pulling force to the line 165, which in turn applies linear pulling force to the proximal nerve end 110, which in turn stimulates nerve regeneration in accordance with the foregoing discussion of the preceding figures. As the proximal nerve end 110 regenerates and lengthens, the drive system 1000 rotates the reel 1010 to provide ongoing regulated tension.

Figure 11:
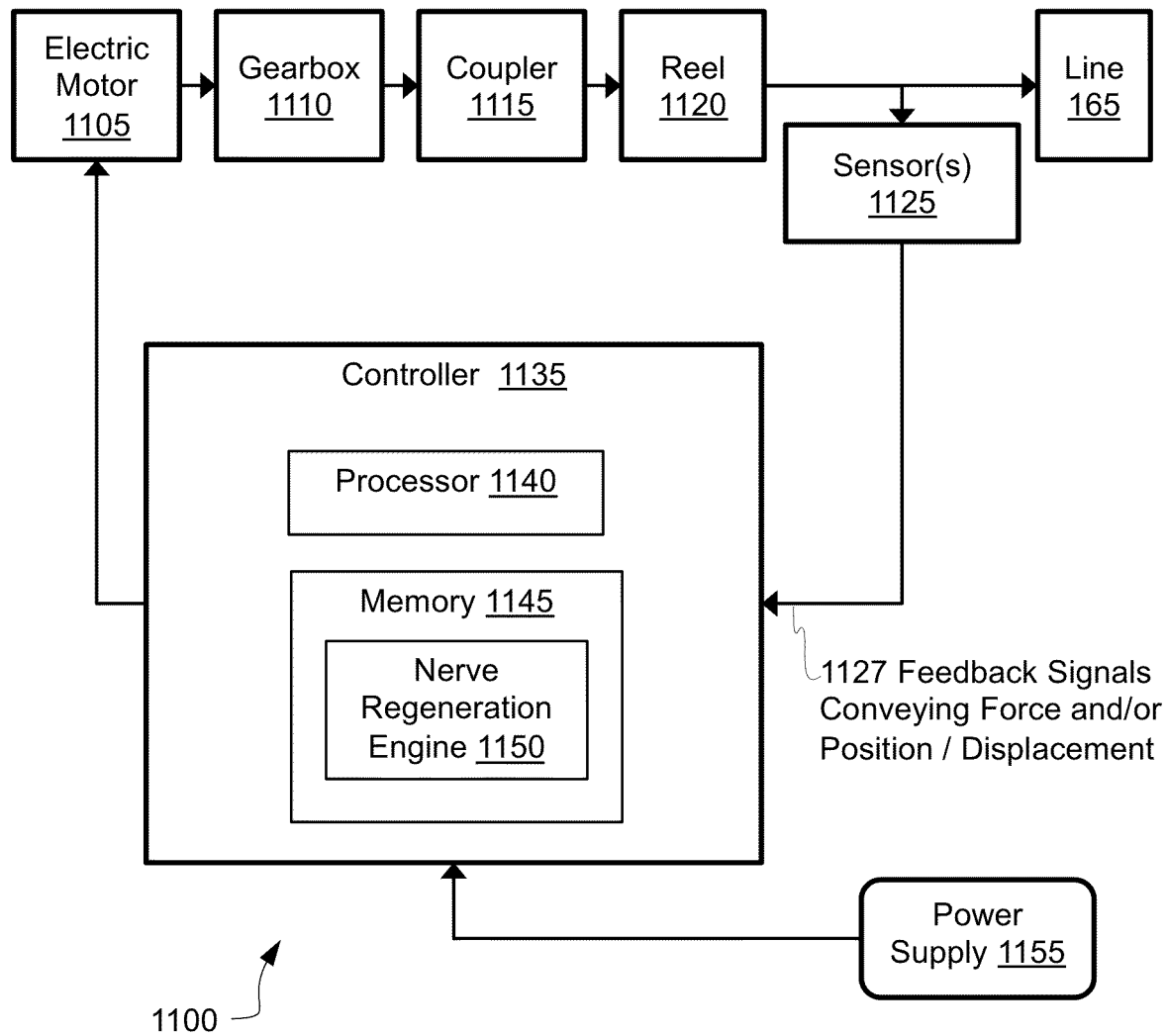
FIG. 11 is an illustration of another regeneration system comprising an electronically controlled motor for delivering tension to injured tissue in accordance with some example embodiments of the disclosure.

Turning now to FIG. 11, this figure illustrates a functional block diagram of an embodiment of a system 1100 for regenerating nerves that employs an electric motor 1105 for reel rotation in place of a spring (or alternatively for use with a spring). The electric motor 1105 is controlled by a controller 1135. The electric motor 1105 delivers force to the line 165, the force is modulated by a gearbox 1110 and is coupled by a coupler 1115 to a reel 1120. One or more sensors 1125 gather feedback signals 1127 which convey force and/or position/displacement information (and/or other physiological information relevant to nerve regeneration) to the controller 1135. These feedback signals 1127 are used by the nerve regeneration engine 1150, which is stored in nonvolatile memory 1145, and an associated processor 1140 to modulate the amount of torque generated by the motor 1105 so as to regulate and/or optimize the tension placed on the proximal nerve end 110 by the line 165.

The nerve regeneration engine 1150 may comprise instructions for executing certain steps of a nerve regeneration process. For example, in some embodiments, the nerve regeneration engine 1150 comprises executable instructions for implementing the loop of blocks 210, 215, 220, 225, 230, 235, 240, and 245 of process 200 as illustrated in flowchart form by FIG. 2 and discussed above. The processor 1140 can comprise a microprocessor, a microcontroller, or other appropriate computing system for executing such an embodiment of the nerve regeneration engine 1150, for example.

As illustrated, power for the system 1100 is supplied by a power supply 1155. In various embodiments, the power supply 1155 may comprise a battery capable of being recharged via inductive coupling through the skin of the patient. The sensors 1125 may comprise a strain gauge, a torque sensor, a force sensor, a displacement sensor or other appropriate sensors for gathering relevant feedback signals 1127.

In one example embodiment, the sensor 1125 comprises a strain gauge that measures the amount of force on the line 165 (as applied to the proximal nerve end 110). In operation, the controller 1135 compares the measured force to a threshold level. If the controller 1135 determines that the measured force is above the threshold level, then the controller 1135 leaves the electrical motor 1105 in an off state, whereby the measured force is maintained and unnecessary energy consumption is avoided. If, on the other hand, the controller 1135 determines that the measured force is below the threshold level, then the controller 1135 turns the electric motor 1105 on, and the electric motor 1105 responds with rotation.

The gearbox 1110 gears down the rotational motion of the electric motor 1105 and comprises a ratchet wheel and pawl that prevents unwanted backward rotation or other appropriate gearing arrangement or means. The gearbox 1110 drives rotation of the reel 1120 via the coupler 1115, which in various embodiments can comprise a rotary damper, a spring, or any link, member, fastener or other means for transmitting force and motion between the gearbox 1110 and the reel 1120 (without limitation). The rotation of the reel 1120 increases force on the line 165 until the controller 1135 determines that the measured force meets the threshold level. Once the threshold level is met, the controller 1135 turns the electric motor 1105 off, and the ratchet wheel and pawl of the gearbox 1110 hold the rotational position of the reel 1120. Once the nerve sufficiently lengthens, the measured force drops below the threshold level, and the controller 1135 again prompts the electrical motor to drive rotation of the reel 1120 until the force threshold is met. In this manner the system 1110 can maintain a target level of force applied to the proximal nerve end 110 while managing energy consumption.

In an example variation, the controller 1135 can utilize a deadband approach for regulating applied force. In this approach, the controller 1135 uses one force threshold for turning the motor on and another force threshold for turning the motor off. The difference between the two thresholds can define a deadband range in which the target force lies.

Technology useful for regenerating tissue has been described. From the description, it will be appreciated that an embodiment of the disclosure overcomes limitations of the prior art. Those skilled in the art will appreciate that the technology is not limited to any specifically discussed application or implementation and that the embodiments described herein are illustrative and not restrictive. Furthermore, the particular features, structures, or characteristics that are set forth may be combined in any suitable manner in one or more embodiments based on this disclosure and ordinary skill. Those of ordinary skill having benefit of this disclosure can make, use, and practice a wide range of embodiments via combining the disclosed features and elements in many permutations without undue experimentation. This disclosure not only includes the illustrated and described embodiments, but also provides a rich and detailed roadmap for creating many additional embodiments using the various disclosed technologies, elements, features, and their equivalents. From the description of the example embodiments, equivalents of the elements shown herein will suggest themselves to those skilled in the art, and ways of constructing other embodiments will appear to practitioners of the art. Therefore, the scope of the technology is to be limited only by the appended claims.

Moreover, those skilled in the art will recognize, or be able to ascertain using their skill, the present teaching, and no more than routine experimentation, many equivalents to the specific embodiments described herein. Such equivalents are intended to be encompassed by the following claims.

All publications, patents, and patent applications mentioned in this specification are herein incorporated by reference into the specification to the same extent as if each individual publication, patent or patent application was specifically indicated to be incorporated herein by reference.

Other embodiments are in the claims.

What is claimed is:

1. A system for stimulating nerve growth in a vertebrate, comprising:
 a housing that is configured for implanting in the vertebrate and attachment to tissue of the vertebrate, that encloses a space, and that comprises an aperture;
 a reel disposed in the enclosed space;
 a line extending through the aperture and having a first end coupled to the reel and a second end configured for surgical attachment to an end of a nerve of the vertebrate;
 a drive disposed in the enclosed space and operably coupled to the reel; and
 a pump system for delivery of one or more pharmaceutical agents or other treatment modalities to the nerve.

2. The system of claim 1, wherein the drive comprises:
 an energy storage system; and
 a linkage operably coupled to the reel and configured to rotate the reel and retract the line using energy from the energy storage system.

3. The system of claim 2, wherein the energy storage system comprises a spring configured to store said energy.

4. The system of claim 2, wherein the energy storage system comprises a battery and the linkage comprises an electric motor.

5. The system of claim 1, wherein the drive comprises a constant force spring or a constant torque spring.

6. The system of claim 1, wherein the drive comprises a spring, and wherein the spring and the reel are coaxially disposed.

7. The system of claim 1, wherein the drive comprises a spring motor.

8. The system of claim 1, wherein the tissue comprises bone,
- wherein the system further comprises a fastener configured for fastening to said bone, and
- wherein the housing comprises a second aperture sized according to the fastener.

9. The system of claim 1,
- wherein the pump system comprises:
  - material comprising at least one of a first pharmaceutical agent that stimulates nerve growth and a second pharmaceutical agent comprising an anesthetic;
  - a pump that is configured to deliver the material to the end of the nerve; and
  - a stent sized to receive the end of the nerve and configured to provide a channel in soft tissue of the vertebrate for growth of the nerve.

10. A distraction neurogenesis system comprising:
- a reel;
- a line comprising a first end operably coupled to the reel and a second end configured for attachment to an end of a nerve for distraction;
- a coupler;
- a drive that the coupler couples to the reel, wherein the drive comprises a regulator configured to apply at least one selected level of distraction to the end of the nerve as the nerve undergoes neurogenesis in response to said distraction; and
- a pump system for delivery of one or more pharmaceutical agents or other treatment modalities to the nerve.

11. The distraction neurogenesis system of claim 10, wherein the regulator comprises a constant force spring or a constant torque spring.

12. The distraction neurogenesis system of claim 10, wherein the regulator comprises a damper.

13. The distraction neurogenesis system of claim 10, wherein the regulator comprises a mechanically implemented feedback control loop.

14. The distraction neurogenesis system of claim 10, further comprising a sensor operably coupled to the line,
- wherein the drive comprises an electrical motor and the regulator comprises a microcontroller or microprocessor configured for receiving an output of the sensor as feedback for operating the electrical motor.

15. The distraction neurogenesis system of claim 10,
- wherein the pump system comprises:
  - a pump;
  - a tube extending from the pump; and
  - an implantable housing,
- wherein the pump is configured to pump a pharmaceutical agent through the tube,
- wherein the pharmaceutical agent is operative to promote neurogenesis, and
- wherein the reel, the drive, the coupler, and at least a portion of the line are disposed in the implantable housing.

* * * * *